US008481485B2

(12) United States Patent
DiMarchi et al.

(10) Patent No.: US 8,481,485 B2
(45) Date of Patent: Jul. 9, 2013

(54) INSULIN ANALOGS

(75) Inventors: Richard D. DiMarchi, Carmel, IN (US);
Jie Han, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 13/130,976

(22) PCT Filed: Dec. 18, 2009

(86) PCT No.: PCT/US2009/068712
§ 371 (c)(1),
(2), (4) Date: May 24, 2011

(87) PCT Pub. No.: WO2010/080606
PCT Pub. Date: Jul. 15, 2010

(65) Prior Publication Data
US 2011/0257091 A1   Oct. 20, 2011

Related U.S. Application Data

(60) Provisional application No. 61/139,221, filed on Dec. 19, 2008.

(51) Int. Cl.
*A61K 38/28* (2006.01)
*A61K 38/00* (2006.01)
*A61K 38/04* (2006.01)
*A61P 5/50* (2006.01)
*A61P 3/08* (2006.01)
*A61P 3/10* (2006.01)
*A61P 7/12* (2006.01)
*C07K 5/00* (2006.01)
*C07K 7/00* (2006.01)
*C07K 16/00* (2006.01)
*C07K 17/00* (2006.01)

(52) U.S. Cl.
USPC ............. 514/6.2; 514/6.3; 514/6.7; 514/6.8; 514/6.9; 530/330

(58) Field of Classification Search
None
See application file for complete search history.

(56) References Cited

U.S. PATENT DOCUMENTS

| | | | |
|---|---|---|---|
| 3,740,385 A | 6/1973 | Ondetti | |
| 4,275,152 A | 6/1981 | Esders et al. | |
| 4,741,897 A | 5/1988 | Andrews et al. | |
| 4,876,242 A | 10/1989 | Applebaum et al. | |
| 4,985,407 A | 1/1991 | Foxton et al. | |
| 5,359,030 A | 10/1994 | Ekwuribe | |
| 5,514,646 A | 5/1996 | Chance et al. | |
| 6,180,767 B1 | 1/2001 | Wickstrom et al. | |
| 6,197,926 B1 * | 3/2001 | Gaur et al. | 530/303 |
| 6,476,290 B1 | 11/2002 | Wright et al. | |
| 6,630,348 B1 | 10/2003 | Lee et al. | |
| 6,746,853 B1 | 6/2004 | Dahiyat et al. | |
| 7,045,337 B2 | 5/2006 | Schultz et al. | |
| 7,326,688 B2 | 2/2008 | O'Harte et al. | |
| 7,521,422 B2 | 4/2009 | Bernard | |
| 2002/0038026 A1 | 3/2002 | Rao et al. | |
| 2002/0160938 A1 | 10/2002 | Brandenburg et al. | |
| 2003/0195147 A1 | 10/2003 | Pillutla et al. | |
| 2003/0204063 A1 | 10/2003 | Gravel et al. | |
| 2004/0054130 A1 | 3/2004 | Ng et al. | |
| 2004/0121940 A1 | 6/2004 | De Groot et al. | |
| 2005/0014679 A1 | 1/2005 | Beals et al. | |
| 2005/0187147 A1 | 8/2005 | Newman et al. | |
| 2006/0171920 A1 | 8/2006 | Shechter et al. | |
| 2006/0210534 A1 | 9/2006 | Lee et al. | |
| 2006/0223753 A1 | 10/2006 | Glass | |
| 2007/0173452 A1 | 7/2007 | DiMarchi et al. | |
| 2007/0224119 A1 | 9/2007 | McTavish | |
| 2008/0113411 A1 | 5/2008 | Sheffer | |
| 2008/0113905 A1 | 5/2008 | DiMarchi et al. | |
| 2008/0125574 A1 | 5/2008 | Sheffer et al. | |
| 2009/0054305 A1 | 2/2009 | Schlein et al. | |
| 2009/0176964 A1 | 7/2009 | Walensky et al. | |
| 2009/0192072 A1 | 7/2009 | Pillutla et al. | |
| 2011/0065633 A1 | 3/2011 | Dimarchi et al. | |
| 2011/0288003 A1 | 11/2011 | Dimarchi et al. | |

FOREIGN PATENT DOCUMENTS

| | | |
|---|---|---|
| EP | 0220958 | 5/1987 |
| EP | 1161452 | 2/2000 |
| EP | 2036539 A1 | 3/2009 |
| EP | 2036923 A1 | 3/2009 |
| WO | 90/12814 | 11/1990 |
| WO | 93/03174 | 2/1993 |
| WO | 1998/11126 | 3/1998 |
| WO | 99/46283 | 9/1999 |
| WO | 02/10195 | 2/2002 |
| WO | 2004/067548 | 8/2004 |
| WO | 2004/078777 | 9/2004 |
| WO | 2005/054291 | 6/2005 |

(Continued)

OTHER PUBLICATIONS

Coy et al., Journal of Medicinal Chemistry, 1973, vol. 16, No. 7, 827-829.*
Yang et al., World J Gastroentero, 2000; 6(3):371-373.*
Hinds et al., Advanced Drug Delivery Reviews 2002, (54) 505-530.*
De, et al., "Investigation of the feasibility of an amide-based prodrug under physiological conditions," Int. J. Pept. Res. Ther., 14, pp. 255-262 (2008).
Madsen, et al., "Structure-activity and protraction relationship of long-acting glucagon-like peptide-1 derivatives: Importance of fatty acid length, polarity, and bulkiness," J. Med. Chem., 50, pp. 6126-6132 (2007).
Mayer et al. Insulin Structure and Function. PeptideScience 2007, 88(5):687-713; 688, Fig 1.
Wang et al. Identification of Site(s) of Insulin Nitration by Peroxynitrite and Characterization of Its Structural Change. Protein & Peptide Letters 2008, 15:1063-1067; Abstract, p. 1066, col. 2.

(Continued)

*Primary Examiner* — Marcela M Cordero Garcia
*Assistant Examiner* — Kaipeen Yang
(74) *Attorney, Agent, or Firm* — Barnes & Thornburg LLP

(57) ABSTRACT

Full potency analogs of insulin are provided wherein the analog comprises a modification of the tyrosine residue at position 19 of the A chain.

22 Claims, 3 Drawing Sheets

FOREIGN PATENT DOCUMENTS

Figure 1:
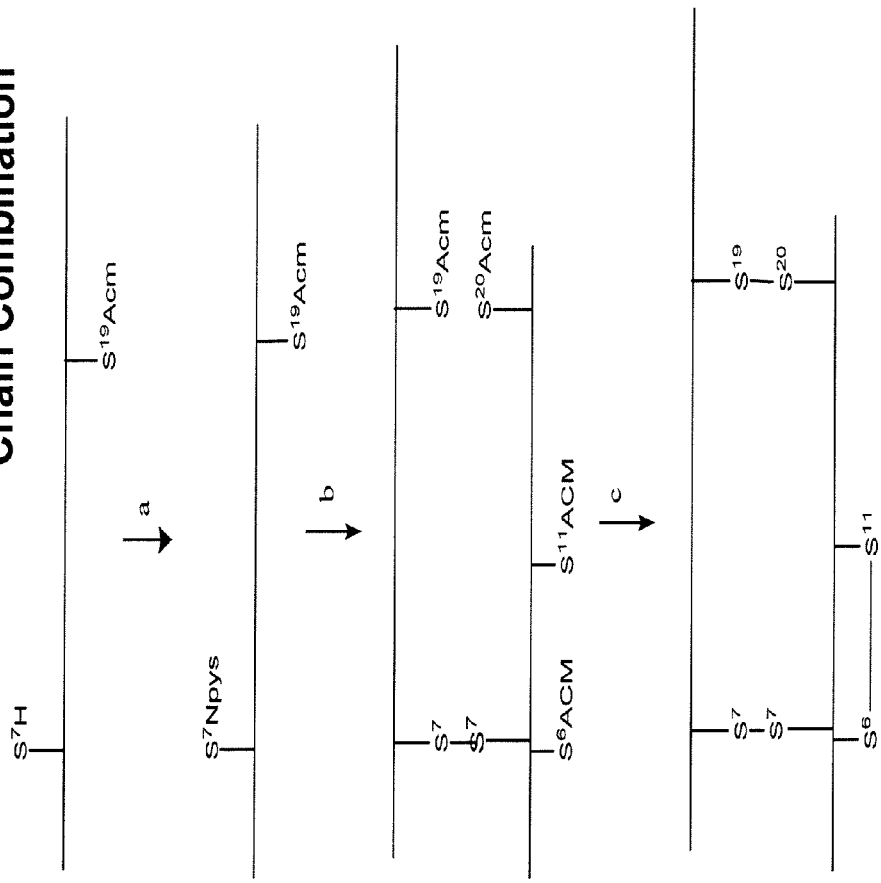

| WO | 2006/047214 | 5/2006 |
|---|---|---|
| WO | 2008/021560 | 2/2008 |
| WO | 2008/025528 | 3/2008 |
| WO | WO2009034118 A1 | 3/2009 |
| WO | WO2009034119 A1 | 3/2009 |
| WO | 2009/067636 | 5/2009 |
| WO | 2009/095479 | 8/2009 |
| WO | WO/2009/099763 | 8/2009 |
| WO | 2010/011313 | 1/2010 |
| WO | 2010/071807 | 6/2010 |
| WO | 2010/080605 | 7/2010 |
| WO | 2011/163012 | 12/2011 |

OTHER PUBLICATIONS

Schilling et al. Degradation of Insulin by Trypsin and Alpha-Chymotrypsin. Pharmaceutical Research 1991, 8(6):721-727; Abstract, p. 727, col. 1.

Kristensen et al. Alanine Scanning Mutagenesis of Insulin. The Journal of Biological Chemistry 1997, 272(20):12978-12983; p. 12982, col. 1, first full para, p. 12982, col. 1, second full para.

Phillips, Nelson B., et al., "Supramolecular Protein Engineering: Design of Zinc-Stapled Insulin Hexamers as a Long Acting Depot," J. Biol. Chem., vol. 285, No. 16, pp. 11755-11759 (Apr. 2010).

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.

Battersby et al., "Diketopiperazine Formation and N-Terminal Degradation in Recombinant Human Growth Hormone", *International Journal of Peptide & Protein Research* 44: 215-222, (1994).

Breiner, M., et al., Heterogeneity of Insulin-Receptors in Rat-Tissues as Detected with the Partial Agonist B29,B29'-Suberoyl-Insulin. Molecular Pharmacology, 1993. 44(2): p. 271-276.

Cheng et al., "The Development of an Insulin-based Prodrug," APS poster presentation, 2011.

Coffman et al., "Insulin-metal ion interactions: the binding of divalent cations to insulin hexamers and tetramers and the assembly of insulin-hexamers," Biochemistry, Aug. 9, 1988, vol. 27, No. 16, pp. 6179-6187.

De et al., Synthesis and characterization of ester-based prodrugs of glucagon-like peptide 1, *Biopolymers*, 94(4): 448-56 (2010).

De, A. and DiMarchi, R. Synthesis & Analysis of Peptide Hormone-based prodrugs, (2009) Proceedings of the 21st American Peptide Society 160-161.

Deppe, C., et al., Structure-Activity Relationship of Covalently Dimerized Insulin Derivatives—Correlation of Partial Agonist Efficacy with Cross-Linkage at Lysine B29. Naunyn-Schmiedebergs Archives of Pharmacology, 1994. 350(2): p. 213-217.

DiMarchi, "Peptides—Development of Prodrug Chemistry," RBF Symposium Feb. 1-4, 2011 India.

Du et al., "Biochemistry and Molecular Biology International," vol. 45, No. 2, Jun. 1, 1998, pp. 255-260 XP008147747.

Du X et al, Hydroxyl group of insulin A19Tyris essential for receptor binding: studies on (A9Phe) insulin, BioChem and Mol Biology International, Academic Press, Lindon, GB vol. 45, No. 2, Jun 1, 1998, pp. 255-260. found in extended EP search report 09837982.9 (08055; 216442).

Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).

European supplemental search report for EP 09837983.7 completed by the EPO on Mar. 15, 2012.

Evans et al., "Effect of β-Endorphin C-Terminal Peptides on Glucose Uptake in Isolated Skeletal Muscles of the Mouse", Peptides, vol. 18, No. 1, pp. 165-167, (1997).

Garcia-Aparicio et al., "Design and Discovery of a Novel Dipeptidyl-peptidase IV (CD26)-Based Prodrug Approach", *J. Med. Chem.* 49: 5339-5351 (2006).

Gershonov et al, A Novel Approach for a Water-Soluble long Acting Insulin Prodrug . . . , J. Med. Chem (2000) vol. 43, pp. 2530-2537.

Goolcharran et al., "Comparison of the Rates of Deamidation, Diketopiperazine Formation, and Oxidation in Recombinant Human Vascular Endothelial Growth Factor and Model Peptides", *AAPS Pharmsci 2000* 2(1) article 5: 1-6 (Mar. 17, 2000).

Hamel et al "Cyclosporin a prodrugs: Design, synthesis and biophysical properties", J. Peptide Research, vol. 63 No. 2 pp. 147-154 (Feb. 2004).

Han et al., "IGF-based Insulin Analogs with an A-Chain Lactam," APS poster presentation, 2011.

Han et al., "Insulin Chemical Synthesis Using a Two-Step Orthogonal Formation of the Disulfides," APS poster presentation.

Han et al., "Structure-Activity Relationship of Insulin at Position $A^{19}$," APS poster presentation.

Harris, J. Milton, Final Word: PEGylation—A "Sunset" Technology? <http://licence.icopyright.net/user/viewFreeUse.act?fuid=OTU1NjT3OA%3D%3D>, BioPharm International, Jun. 1, 2004.

Hua et al., "Design of an active ultrastable single-chain insulin analog," J. of Biological Chemistry, Mar. 2008, vol. 283, No. 21, 14703-14716.

Joost, H.G., et al., Quantitative Dissociation of Glucose-Transport Stimulation and Insulin-Receptor Tyrosine Kinase Activation in Isolated Adipocytes with a Covalent Insulin Dimer (B29,B29'-Sunberoyl-Insulin). Biochemical Pharmacology, 1989. 38(14): p. 2269-2277.

Kaur et al., "Chemical Synthesis of Insulin and Related Analogs," APS poster presentation.

Kaur et al., "Novel Single Chain Insulin Analogs Consisting of a Non-Peptide Based Connection," APS poster presentation, May 12, 2011.

Kurapkat et al "Inactive conformation of an insulin despite its wild-type sequence", Protein Science, vol. 6, No. 3, pp. 580-587 (Mar. 1997).

M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

Mayer et al., Insulin Structure and Function, Peptide Science 2007, 88(5):687-713.

Mroz, Piotr et al., "Bioactivity of Insulin Analogs with Altered B-Chain Secondary Structure," APS poster presentation.

O'Brien, Assay for DPPIV Activity using a Homogenous, Luminescent Method, Cell Notes, 2005, 11:8-11 (http://www.promega.com/resources/articles/pubhub/cellnotes/assay-for-dppiv-activity-using-a-homogeneous-luminescent-method/).

PCT International Search Report for PCT/US2009/068711 completed by the US Searching Authority on Feb. 4, 2010.

PCT International Search Report for PCT/US2009/068712 completed by the US Searching Authority on Mar. 24, 2010.

PCT International Search Report for PCT/US2009/068713.

PCT International Search Report for PCT/US2009/068716 completed by the US Searching Authority on May 3, 2010.

PCT International Search Report for PCT/US2009/068745 completed by the US Searching Authority on Feb. 1, 2010.

Quan et al., "Coordinated Interaction of the Insulin B-chain Helical Domain with the aromatic Active Site," APS poster presentation.

Roth, R.A., et al., Effects of Covalently Linked Insulin Dimers on Receptor Kinase-Activity and Receptor down Regulation. Febs Letters, 1984. 170(2): p. 360-364.

Santos et al., Cyclization-Activated Prodrugs. Synthesis, Reactivity and Toxicity of Dipeptide Esters of Paracetamol, *Bioorganic & Medicinal Chemistry Letters* 15: 1595-1598 (2005).

Sato, H., "Enzymatic procedure for site-specific pegylation of proteins," Advanced Drug Delivery Reviews 54, pp. 487-504 (2002).

Schilling et al., "Degradation of Insulin by Trypsin and Alphachymotrypsin," Pharmaceutical Research 1991, 8(6):721-727 (abstract).

Schuttler, A. and D. Brandenburg, Preparation and Properties of Covalently Linked Insulin Dimers. Hoppe-Seylers Zeitschrift Fur Physiologische Chemie, 1982. 363(3): p. 317-330.

Shojaee-Moradie, F., et al., Demonstration of a Relatively Hepatoselective Effect of Covalent Insulin Dimers on Glucose-Metabolism in Dogs. Diabetologia, 1995. 38(9): p. 1007-1013.

Tatnell, M.A., et al., Evidence Concerning the Mechanism of Insulin-Receptor Interaction and the Structure of the Insulin-Receptor from Biological Properties of Covalently Linked Insulin Dimers. Biochemical Journal, 1983. 216(3): p. 687-694.

Tatnell, M.A., R.H. Jones, and P.H. Sonksen, Covalently-Linked Insulin Dimers—Their Metabolism and Biological Effects Invivo as Partial Competitive Antagonists of Insulin-Clearance. Diabetologia, 1984. 27(1): p. 27-31.

Wang et al., "Identification of Site(s) of Insulin Nitration by Peroxynitrite and Characterization of its Structural Change," Protein & Peptide Letters 2008, 15:1063-1067.

Ward, "Fatty Acid Acylation of Peptides: Developing strategies to enhance medicines for treating metabolic disorders," Jan. 14, 2009.

Weiland et al, "Antagonistic effects of a covalently dimerized insulin derivatized insulin derivative on insulin receptors in 3T3-L1 adipocytes", PNAS, vol. 87, pp. 1154-1158, Feb. 1990.

Yang et al., "A Novel Approach to Resin-Based Cysteine Alkylation," American Peptide Society, 2005.

Zhao et al., "Improved Pharmacokinetics through Site-Specific PEGylation of Insulin Analogs," APS poster presentation, 2011.

De, Design of peptide-based prodrug chemistry and its application to glucagon-like peptide 1. Masters Thesis Aug. 2007. [Retrieved from the Internet on Jun. 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2, p. 79, para 1.

GenBank entry AAH05278, Jul. 15, 2006 [http:www/ncbi.nim.nih.gov/protein/13528972>].

PCT International Search Report for PCT/US2011/041601 completed by the US Searching Authority on Nov. 10, 2011.

PCT International Search Report for PCT/US2009/031593 completed by the US Searching Authority on Jul. 16, 2009.

Danho et al., "[A-19-Phenylalanine] Insulin: A New Synthetic Analogue," Hoppe-Seyler's Z. Physiol. Chem.,Bd. 361, S. 735-746, May 1980.

* cited by examiner

Synthetic "A⁷-B⁷"-derived Insulin Receptor Binding

SEQUENCE LISTING

<160> NUMBER OF SEQ ID NOS: 52

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine or histidine
<220> FEATURE:
<221> NAME/KEY: MISC_FEATURE
<222> LOCATION: (19)..(19)
<223> OTHER INFORMATION: Xaa at position 19 is 4-amino phenylalanine or
      4-methoxy phenylalanine
<220> FEATURE:
<221> NAME/KEY: MISC_FEATURE
<222> LOCATION: (21)..(21)
<223> OTHER INFORMATION: Xaa at position 21 is asparagine, glycine,
      alanine, glutamine, glutamate, threonine, or serine

<400> SEQUENCE: 3

Gly Ile Val Glu Gln Cys Cys Xaa Ser Ile Cys Ser Leu Tyr Gln Leu
1               5                   10                  15

Glu Asn Xaa Cys Xaa
            20

<210> SEQ ID NO 4
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 4

Xaa Leu Cys Gly Xaa Xaa Leu Val Glu Ala Leu Tyr Leu Val Cys Gly
1               5                   10                  15

Glu Arg Gly Phe Phe

<210> SEQ ID NO 5
<211> LENGTH: 30
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or
      desamino-phenylalanine.
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
<220> FEATURE:
<221> NAME/KEY: MISC_FEATURE
<222> LOCATION: (30)..(30)
<223> OTHER INFORMATION: Xaa at position 30 is threonine or alanine

<400> SEQUENCE: 5

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Asp Lys Xaa
            20                  25                  30

<210> SEQ ID NO 6
<211> LENGTH: 21
<212> TYPE: PRT
<213> ORGANISM: Artificial Sequence
<220> FEATURE:
<223> OTHER INFORMATION: Analog of insulin a chain
<220> FEATURE:
<221> NAME/KEY: MISC_FEATURE
<222> LOCATION: (19)..(19)
<223> OTHER INFORMATION: Xaa at position 19 is 4-amino phenylalanine

<400> SEQUENCE: 6

Gly Ile Val Glu Gln Cys Cys Thr Ser Ile Cys Ser Leu Tyr Gln Leu
1               5                   10                  15

Glu Asn Xaa Cys Asn
            20

<210> SEQ ID NO 7
<211> LENGTH: 21
<212> TYPE: PRT
<213> ORGANISM: Homo sapiens

<400> SEQUENCE: 7

His Leu Cys Gly Ser His Leu Val Glu Ala Leu Tyr Leu Val Cys Gly
1               5                   10                  15

Glu Arg Gly Phe Phe
            20

<210> SEQ ID NO 8
<211> LENGTH: 30
<212> TYPE: PRT
<213> ORGANISM: Homo sapiens

```
<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 9
<211> LENGTH: 30
<212> TYPE: PRT
<213> ORGANISM: Homo sapiens

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 10
<211> LENGTH: 32
<212> TYPE: PRT
<213> ORGANISM: Homo sapiens

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 11
<211> LENGTH: 7
<212> TYPE: PRT
<213> ORGANISM: Artificial Sequence
<220> FEATURE:
<223> OTHER INFORMATION: peptide linker

<400> SEQUENCE: 11

Gly Gly Gly Pro Gly Lys Arg
1               5

<210> SEQ ID NO 12
<211> LENGTH: 12
<212> TYPE: PRT
<213> ORGANISM: Artificial Sequence
<220> FEATURE:
<223> OTHER INFORMATION: peptide linker

<400> SEQUENCE: 12

Gly Tyr Gly Ser Ser Ser Arg Arg Ala Pro Gln Thr
1               5                   10

<210> SEQ ID NO 13
<211> LENGTH: 7
<212> TYPE: PRT
<213> ORGANISM: Artificial Sequence
<220> FEATURE:
<223> OTHER INFORMATION: peptide linker

<400> SEQUENCE: 13

Gly Gly Gly Gly Gly Lys Arg
1               5

<210> SEQ ID NO 14
<211> LENGTH: 7
<212> TYPE: PRT
<213> ORGANISM: Artificial Sequence
```

```
<220> FEATURE:
<223> OTHER INFORMATION: peptide linker

<400> SEQUENCE: 14

Arg Arg Gly Gly Gly Gly Gly
1               5

<210> SEQ ID NO 15
<211> LENGTH: 9
<212> TYPE: PRT
<213> ORGANISM: Artificial Sequence
<220> FEATURE:
<223> OTHER INFORMATION: peptide linker

<400> SEQUENCE: 15

Gly Gly Ala Pro Gly Asp Val Lys Arg
1               5

<210> SEQ ID NO 16
<211> LENGTH: 9
<212> TYPE: PRT
<213> ORGANISM: Artificial Sequence
<220> FEATURE:
<223> OTHER INFORMATION: peptide linker

<400> SEQUENCE: 16

Arg Arg Ala Pro Gly Asp Val Gly Gly
1               5

<210> SEQ ID NO 17
<211> LENGTH: 9
<212> TYPE: PRT
<213> ORGANISM: Artificial Sequence
<220> FEATURE:
<223> OTHER INFORMATION: peptide linker

<400> SEQUENCE: 17

Gly Gly Tyr Pro Gly Asp Val Lys Arg
1               5

<210> SEQ ID NO 18
<211> LENGTH: 9
<212> TYPE: PRT
<213> ORGANISM: Artificial Sequence
<220> FEATURE:
<223> OTHER INFORMATION: peptide linker

<400> SEQUENCE: 18

Arg Arg Tyr Pro Gly Asp Val Gly Gly
1               5

<210> SEQ ID NO 19
<211> LENGTH: 9
<212> TYPE: PRT
<213> ORGANISM: Artificial Sequence
<220> FEATURE:
<223> OTHER INFORMATION: peptide linker

<400> SEQUENCE: 19

Gly Gly His Pro Gly Asp Val Lys Arg
1               5

<210> SEQ ID NO 20
<211> LENGTH: 9
<212> TYPE: PRT
<213> ORGANISM: Artificial Sequence
<220> FEATURE:
<223> OTHER INFORMATION: peptide linker
```

```
<400> SEQUENCE: 20

Arg Arg His Pro Gly Asp Val Gly Gly
1               5

<210> SEQ ID NO 21
<211> LENGTH: 7
<212> TYPE: PRT
<213> ORGANISM: Artificial Sequence
<220> FEATURE:
<223> OTHER INFORMATION: peptide linker

<400> SEQUENCE: 21

Arg Arg Gly Pro Gly Gly Gly
1               5

<210> SEQ ID NO 22
<211> LENGTH: 51
<212> TYPE: PRT
<213> ORGANISM: Artificial Sequence
<220> FEATURE:
<223> OTHER INFORMATION: single chain human insulin analog
<220> FEATURE:
<221> NAME/KEY: MISC_FEATURE
<222> LOCATION: (49)..(49)
<223> OTHER INFORMATION: Xaa at position 49 is 4-amino phenylalanine or
      4-methoxy phenylalanine

<400> SEQUENCE: 22

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Ile
            20                  25                  30

Val Glu Gln Cys Cys Thr Ser Ile Cys Ser Leu Tyr Gln Leu Glu Asn
        35                  40                  45

Xaa Cys Asn
    50

<210> SEQ ID NO 23
<211> LENGTH: 63
<212> TYPE: PRT
<213> ORGANISM: Artificial Sequence
<220> FEATURE:
<223> OTHER INFORMATION: single-chain human insulin analog
<220> FEATURE:
<221> NAME/KEY: MISC_FEATURE
<222> LOCATION: (61)..(61)
<223> OTHER INFORMATION: Xaa at position 61 is 4-amino phenylalanine or
      4-methoxy phenylalanine

<400> SEQUENCE: 23

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gln Pro
            20                  25                  30

Leu Ala Leu Glu Gly Ser Leu Gln Lys Arg Gly Ile Val Glu Gln Cys
        35                  40                  45

Cys Thr Ser Ile Cys Ser Leu Tyr Gln Leu Glu Asn Xaa Cys Asn
    50                  55                  60

<210> SEQ ID NO 24
<211> LENGTH: 7
<212> TYPE: PRT
<213> ORGANISM: Artificial Sequence
<220> FEATURE:
<223> OTHER INFORMATION: peptide linker
```

```
<400> SEQUENCE: 24

Ala Gly Arg Gly Ser Gly Lys
1               5

<210> SEQ ID NO 25
<211> LENGTH: 7
<212> TYPE: PRT
<213> ORGANISM: Artificial Sequence
<220> FEATURE:
<223> OTHER INFORMATION: peptide linker

<400> SEQUENCE: 25

Ala Gly Leu Gly Ser Gly Lys
1               5

<210> SEQ ID NO 26
<211> LENGTH: 7
<212> TYPE: PRT
<213> ORGANISM: Artificial Sequence
<220> FEATURE:
<223> OTHER INFORMATION: peptide linker

<400> SEQUENCE: 26

Ala Gly Met Gly Ser Gly Lys
1               5

<210> SEQ ID NO 27
<211> LENGTH: 7
<212> TYPE: PRT
<213> ORGANISM: Artificial Sequence
<220> FEATURE:
<223> OTHER INFORMATION: peptide linker

<400> SEQUENCE: 27

Ala Ser Trp Gly Ser Gly Lys
1               5

<210> SEQ ID NO 28
<211> LENGTH: 7
<212> TYPE: PRT
<213> ORGANISM: Artificial Sequence
<220> FEATURE:
<223> OTHER INFORMATION: peptide linker

<400> SEQUENCE: 28

Thr Gly Leu Gly Ser Gly Gln
1               5

<210> SEQ ID NO 29
<211> LENGTH: 7
<212> TYPE: PRT
<213> ORGANISM: Artificial Sequence
<220> FEATURE:
<223> OTHER INFORMATION: peptide linker

<400> SEQUENCE: 29

Thr Gly Leu Gly Arg Gly Lys
1               5

<210> SEQ ID NO 30
<211> LENGTH: 7
<212> TYPE: PRT
<213> ORGANISM: Artificial Sequence
<220> FEATURE:
<223> OTHER INFORMATION: peptide linker

<400> SEQUENCE: 30
```

Thr Gly Leu Gly Ser Gly Lys
1               5

<210> SEQ ID NO 31
<211> LENGTH: 7
<212> TYPE: PRT
<213> ORGANISM: Artificial Sequence
<220> FEATURE:
<223> OTHER INFORMATION: peptide linker

<400> SEQUENCE: 31

His Gly Leu Tyr Ser Gly Lys
1               5

<210> SEQ ID NO 32
<211> LENGTH: 7
<212> TYPE: PRT
<213> ORGANISM: Artificial Sequence
<220> FEATURE:
<223> OTHER INFORMATION: peptide linker

<400> SEQUENCE: 32

Lys Gly Leu Gly Ser Gly Gln
1               5

<210> SEQ ID NO 33
<211> LENGTH: 7
<212> TYPE: PRT
<213> ORGANISM: Artificial Sequence
<220> FEATURE:
<223> OTHER INFORMATION: peptide linker

<400> SEQUENCE: 33

Val Gly Leu Met Ser Gly Lys
1               5

<210> SEQ ID NO 34
<211> LENGTH: 7
<212> TYPE: PRT
<213> ORGANISM: Artificial Sequence
<220> FEATURE:
<223> OTHER INFORMATION: peptide linker

<400> SEQUENCE: 34

Val Gly Leu Ser Ser Gly Gln
1               5

<210> SEQ ID NO 35
<211> LENGTH: 7
<212> TYPE: PRT
<213> ORGANISM: Artificial Sequence
<220> FEATURE:
<223> OTHER INFORMATION: peptide linker

<400> SEQUENCE: 35

Val Gly Leu Tyr Ser Gly Lys
1               5

<210> SEQ ID NO 36
<211> LENGTH: 7
<212> TYPE: PRT
<213> ORGANISM: Artificial Sequence
<220> FEATURE:
<223> OTHER INFORMATION: peptide linker

<400> SEQUENCE: 36

Val Gly Leu Ser Ser Gly Lys

<210> SEQ ID NO 37
<211> LENGTH: 7
<212> TYPE: PRT
<213> ORGANISM: Artificial Sequence
<220> FEATURE:
<223> OTHER INFORMATION: peptide linker

<400> SEQUENCE: 37

Val Gly Met Ser Ser Gly Lys
1               5

<210> SEQ ID NO 38
<211> LENGTH: 7
<212> TYPE: PRT
<213> ORGANISM: Artificial Sequence
<220> FEATURE:
<223> OTHER INFORMATION: peptide linker

<400> SEQUENCE: 38

Val Trp Ser Ser Ser Gly Lys
1               5

<210> SEQ ID NO 39
<211> LENGTH: 7
<212> TYPE: PRT
<213> ORGANISM: Artificial Sequence
<220> FEATURE:
<223> OTHER INFORMATION: peptide linker

<400> SEQUENCE: 39

Val Gly Ser Ser Ser Gly Lys
1               5

<210> SEQ ID NO 40
<211> LENGTH: 7
<212> TYPE: PRT
<213> ORGANISM: Artificial Sequence
<220> FEATURE:
<223> OTHER INFORMATION: peptide linker

<400> SEQUENCE: 40

Val Gly Met Ser Ser Gly Lys
1               5

<210> SEQ ID NO 41
<211> LENGTH: 7
<212> TYPE: PRT
<213> ORGANISM: Artificial Sequence
<220> FEATURE:
<223> OTHER INFORMATION: peptide linker

<400> SEQUENCE: 41

Thr Gly Leu Gly Ser Gly Arg
1               5

<210> SEQ ID NO 42
<211> LENGTH: 7
<212> TYPE: PRT
<213> ORGANISM: Artificial Sequence
<220> FEATURE:
<223> OTHER INFORMATION: peptide linker

<400> SEQUENCE: 42

Thr Gly Leu Gly Lys Gly Gln
1               5

```
<210> SEQ ID NO 43
<211> LENGTH: 7
<212> TYPE: PRT
<213> ORGANISM: Artificial Sequence
<220> FEATURE:
<223> OTHER INFORMATION: peptide linker

<400> SEQUENCE: 43

Lys Gly Leu Ser Ser Gly Gln
1               5

<210> SEQ ID NO 44
<211> LENGTH: 7
<212> TYPE: PRT
<213> ORGANISM: Artificial Sequence
<220> FEATURE:
<223> OTHER INFORMATION: peptide linker

<400> SEQUENCE: 44

Val Lys Leu Ser Ser Gly Gln
1               5

<210> SEQ ID NO 45
<211> LENGTH: 7
<212> TYPE: PRT
<213> ORGANISM: Artificial Sequence
<220> FEATURE:
<223> OTHER INFORMATION: peptide linker

<400> SEQUENCE: 45

Val Lys Leu Ser Ser Gly Gln
1               5

<210> SEQ ID NO 46
<211> LENGTH: 7
<212> TYPE: PRT
<213> ORGANISM: Artificial Sequence
<220> FEATURE:
<223> OTHER INFORMATION: peptide linker

<400> SEQUENCE: 46

Thr Gly Leu Gly Lys Gly Gln
1               5

<210> SEQ ID NO 47
<211> LENGTH: 7
<212> TYPE: PRT
<213> ORGANISM: Artificial Sequence
<220> FEATURE:
<223> OTHER INFORMATION: peptide linker

<400> SEQUENCE: 47

Val Gly Leu Ser Lys Gly Gln
1               5

<210> SEQ ID NO 48
<211> LENGTH: 30
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or
      desamino-phenylalanine.
<220> FEATURE:
<221> NAME/KEY: MISC_FEATURE
<222> LOCATION: (5)..(5)
```

-continued

```
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
<220> FEATURE:
<221> NAME/KEY: MISC_FEATURE
<222> LOCATION: (30)..(30)
<223> OTHER INFORMATION: Xaa at position 30 is threonine or alanine

<400> SEQUENCE: 48

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Lys Pro Xaa
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or
      desamino-phenylalanine.
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
<220> FEATURE:
<221> NAME/KEY: MISC_FEATURE
<222> LOCATION: (30)..(30)
<223> OTHER INFORMATION: Xaa at position 30 is threonine or alanine

<400> SEQUENCE: 49

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Pro Lys Xaa
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or
      desamino-phenylalanine.
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
```

-continued

<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 50

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Asp Lys Thr Arg Arg
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or
      desamino-phenylalanine.
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 51

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Lys Pro Thr Arg Arg
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or
      desamino-phenylalanine.
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 52

Xaa Val Asn Gln Xaa Leu Cys Gly Xaa Xaa Leu Val Glu Ala Leu Tyr
1               5                   10                  15

```
Leu Val Cys Gly Glu Arg Gly Phe Phe Tyr Thr Pro Lys Thr Arg Arg
         20                  25                  30
```

INSULIN ANALOGS

CROSS REFERENCE TO RELATED APPLICATIONS

This application is a U.S. national counterpart application of international application serial No. PCT/US2009/068712 filed Dec. 18, 2009, which claims priority to U.S. Provisional Patent Application No. 61/139,221 filed Dec. 19, 2008. The entire disclosures of PCT/US2009/068712 and U.S. Ser. No. 61/139,221 are hereby incorporated by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 17 KB ACII (Text) file named insulinanalogSEQListrevised.txt created on Jan. 27, 2010.

BACKGROUND

Insulin is a miraculous peptide hormone. It demonstrates unparalleled ability to lower glucose in virtually all forms of diabetes. Unfortunately, its pharmacology is not glucose sensitive and as such it is capable of excessive action that can lead to life-threatening hypoglycemia. Inconsistent pharmacology is a hallmark of insulin therapy such that it is extremely difficult to normalize blood glucose without occurrence of hypoglycemia. Furthermore, native insulin is of short duration of action and requires modification to render it suitable for use in control of basal glucose. One central goal in insulin therapy is designing an insulin formulation capable of providing a once a day time action. Extending the action time of an insulin dosage can be achieved by decreasing the solubility of insulin at the site of injection.

There are three proven and distinct molecular approaches to reducing solubility and they include; (1) formulation of insulin as an insoluble suspension with zinc, (2) increase in its isoelectric point to physiological pH through addition of cationic amino acids, (3) covalent modification to provide a hydrophobic ligand that reduces solubility and binds albumin. All of these approaches are limited by the inherent variability that occurs with precipitation at the site of injection, and with subsequent re-solubilization & transport to blood as an active hormone.

Prodrug chemistry offers an alternative mechanism to precisely control the onset and duration of insulin action after clearance from the site of administration and equilibration in the plasma at a highly defined concentration. The central virtue of such an approach relative to current long-acting insulin analogs and formulations is that the insulin reservoir is not the subcutaneous fatty tissue where injection occurs, but rather the blood compartment. This removes the variability in precipitation and solubilization. It also enables administration of the peptide hormone by routes other than a subcutaneous injection. To build a successful prodrug-hormone, an active site structural address is needed that can form the basis for the reversible attachment of a prodrug structural element. The structural address needs to offer two key features; (1) the potential for selective chemical modification and (2) the ability to provide full activity in the native form upon removal of the prodrug structural element.

Insulin is a two chain heterodimer that is biosynthetically derived from a low potency single chain proinsulin precursor through enzymatic processing. Human insulin is comprised of two peptide chains (an "A chain" (SEQ ID NO: 1) and "B chain" (SEQ ID NO: 2)) bound together by disulfide bonds and having a total of 51 amino acids. The C-terminal region of the B-chain and the two terminal ends of the A-chain associate in a three-dimensional structure to assemble a site for high affinity binding to the insulin receptor. The native insulin structure has limited unique chemical elements at the active site residues that might be used for selective assemble of an amide linked prodrug element. Two sites that could be modified to provide elements for the attachment of a prodrug element include the tyrosine residue at position 19 of the native A chain (the "A19 tyrosine") and the phenylalanine residue at position 24 of the native B chain (the "B24 phenylalanine"). Both of these two amino acids are of central importance in insulin action. However, these two amino acids have also proven highly restrictive in the type of structural change that can be introduced and still maintain full potency.

As disclosed herein applicants have discovered full potency insulin analogs that have been modified at position A19 and could potentially be used to assemble an insulin prodrug derivative.

SUMMARY

In accordance with one embodiment a full potency insulin analog is provided wherein an amino group is inserted into the peptide within the active site of insulin without loss in potency. More particularly, the selective insertion of a 4-amino phenylalanine amino acid moiety for the native tyrosine at position 19 of the A chain can be accommodated without loss in potency of the insulin peptide. Subsequent chemical amidation of this active site amino group with specific dipeptides dramatically lessens activity and serves as a suitable prodrug.

In accordance with one embodiment an insulin analog is provided wherein the A chain of the insulin peptide comprises the sequence GIVEQCCX$_1$SICSLYQLENX$_2$CX$_3$ (SEQ ID NO: 3) and the B chain comprising the sequence X$_4$LCGX$_5$X$_6$LVEALYLVCG ERGFF (SEQ ID NO: 4) wherein X$_1$ is selected from the group consisting of threonine and histidine;

X$_2$ is an amino acid of the general structure $$-HN-CH(CH_2-C_6H_4-R_4)-C(=O)-$$

wherein R$_4$ is —NH$_2$ or OCH$_3$;

X$_3$ is asparagine or glycine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid. In a further embodiment the B chain comprises the sequence $X_{11}$ VNQ$X_4$LCG$X_5X_6$LVEALYLVCGERGFFYT$X_9$ $X_{10}$ (SEQ ID NO: 5) wherein $X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_9$ is aspartate-lysine dipeptide, a lysine-proline dipeptide, or a proline-lysine dipeptide;

$X_{10}$ is threonine, alanine or a theonine-arginine-arginine tripeptide;

$X_{11}$ is selected from the group consisting of phenylalanine and desamino-phenylalanine.

In accordance with one embodiment an insulin analog is provided wherein the A chain of the insulin peptide comprises the sequence GIVEQCCTSICSLYQLEN$X_2$CN (SEQ ID NO: 6) and the B chain comprising a sequence selected from the group consisting of HLCGSHLVEALYLVCGERGFF (SEQ ID NO: 7), FVNQHLCGSHLVEALYLVCGERGFFYTPKT (SEQ ID NO: 8) and FVNQHLCGSHLVEALYLVCGERGFFYTKPT (SEQ ID NO: 9) wherein $X_2$ is an amino acid of the general structure 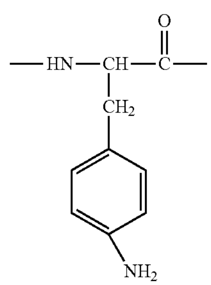 In accordance with one embodiment single-chain A19 insulin analogs are provided. In this embodiment the carboxy terminus of the human insulin B chain, or a functional analog thereof, is covalently linked to the N-terminus of an A19 A chain analog of the present disclosure. In one embodiment the B chain is linked to the A chain via peptide linker of 4-12 or 4-8 amino acids.

In another embodiment the solubility of the insulin analogs is enhanced by the covalent linkage of a hydrophilic moiety to the peptide. In one embodiment the hydrophilic moiety is linked to either the N-terminal amino acid of the B chain or to the amino acid at position 28 of SEQ ID NO: 9 or the amino acid at position 29 of SEQ ID NO: 8. In one embodiment the hydrophilic moiety is a polyethylene glycol (PEG) chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons.

Acylation or alkylation can increase the half-life of the insulin peptides in circulation. Acylation or alkylation can advantageously delay the onset of action and/or extend the duration of action at the insulin receptors. The insulin analogs may be acylated or alkylated at the same amino acid position where a hydrophilic moiety is linked, or at a different amino acid position.

In accordance with one embodiment a pharmaceutical composition is provided comprising any of the novel A19 insulin analogs disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an A19 insulin analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment an improved method of regulating blood glucose levels in insulin dependent patients is provided. The method comprises the steps of administering an A19 insulin analog of the present disclosure in an amount therapeutically effective for the control of diabetes. In one embodiment the A19 insulin analog is pegylated with a PEG chain having a molecular weight selected from the range of about 5,000 to about 40,000 Daltons

BRIEF DESCRIPTION OF THE DRAWINGS

FIG. 1 is a schematic overview of the two step synthetic strategy for preparing human insulin. Details of the procedure are provided in Example 1, step a reagents including 2,2' dithiobis(5-nitropyridin), DMSO at room temperature; step b reagents includeing insulin A (Acm at positions 6, 11 and 20 and SH at position 7), DMSO at room temperature; step c reagents $I_2$ 80% AcOH.

FIG. 2 is a graph comparing the specific binding of the synthetic human insulin relative to purified native insulin to the insulin receptor. As indicated by the results the two molecules have similar binding activities.

FIG. 3 is a graph comparing relative insulin receptor binding of native insulin and the A19 insulin analog (Insulin(p-$NH_2$—F)$^{19}$).

DETAILED DESCRIPTION

Definitions

In describing and claiming the invention, the following terminology will be used in accordance with the definitions set forth below.

As used herein, the term "prodrug" is defined as any compound that undergoes chemical modification before exhibiting its pharmacological effects.

A "bioactive polypeptide" refers to polypeptides which are capable of exerting a biological effect in vitro and/or in vivo.

Designation of an amino acid without specifying its stereochemistry is intended to encompass either the L or D form of the amino acid or a racemic mixture.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of an insulin analog refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

As used herein the term "insulin peptide" is a generic term that designates the 51 amino acid heterodimer comprising the A chain of SEQ ID NO: 1 and the B chain of SEQ ID NO: 2, as well as single-chain insulin analogs thereof (including for example those disclosed in published international application WO96/34882 and U.S. Pat. No. 6,630,348, the disclosures of which are incorporated herein by reference), including heterodimers and single-chain analogs that comprise modified derivatives of the native A chain and/or B chain, including modification of the amino acid at position A19, B16 or B25 to a 4-amino phenylalanine or one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30.

As used herein, the term "single-chain insulin analog" encompasses a group of structurally-related proteins wherein the insulin A and B chains are covalently linked by a polypeptide linker.

An "A19 A chain analog" as used herein designates an amino acid comprising the A chain of SEQ ID NO: 6 and modified derivatives of SEQ ID NO: 6 including one or more amino acid substitutions at positions selected from A5, A8, A9, A10, A12, A14, A15, A17, A18, A21

An "A19 insulin analog" is an insulin peptide that has a substitution of 4-amino phenylalanine or 4-methoxy phenylalanine for the native tyrosine residue at position 19 of the A chain of native insulin.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue. Throughout the application, all references to a particular amino acid position by letter and number (e.g. position A5) refer to the amino acid at that position of either the A chain (e.g. position A5) or the B chain (e.g. position B5) in the respective native human insulin A chain (SEQ ID NO: 1) or B chain (SEQ ID NO: 2), or the corresponding amino acid position in any analogs thereof. For example, a reference herein to "position B28" absent any further elaboration would mean the corresponding position B27 of the B chain of an insulin analog in which the first amino acid of SEQ ID NO: 2 has been deleted.

As used herein, the term "conservative amino acid substitution" is defined herein as exchanges within one of the following five groups:

I. Small Aliphatic, Nonpolar or Slightly Polar Residues:
Ala, Ser, Thr, Pro, Gly;
II. Polar, Negatively Charged Residues and their Amides:
Asp, Asn, Glu, Gln;
III. Polar, Positively Charged Residues:
H is, Arg, Lys; Ornithine (Orn)
IV. Large, Aliphatic, Nonpolar Residues:
Met, Leu, Ile, Val, Cys, Norleucine (Nle), homocysteine
V. Large, Aromatic Residues:
Phe, Tyr, Trp, acetyl phenylalanine As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 80,000 Daltons. "Polyethylene glycol chain" or "PEG chain" is used in combination with a numeric suffix to indicate the approximate average molecular weight thereof. For example, PEG-5,000 refers to polyethylene glycol chain having a total molecular weight average of about 5,000 Daltons.

As used herein the term "pegylated" and like terms refers to a compound that has been modified from its native state by linking a polyethylene glycol chain to the compound. A "pegylated polypeptide" is a polypeptide that has a PEG chain covalently bound to the polypeptide.

As used herein a "linker" is a bond, molecule or group of molecules that binds two separate entities to one another.

Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl ($—CH_2—CH=CH_2$), 1,3-butadienyl, ($—CH=CHCH=CH_2$), 1-butenyl ($—CH=CHCH_2CH_3$), hexenyl, pentenyl, and the like.

The term "$C_2$-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "($C_1$-$C_3$ alkyl)($C_6$-$C_{10}$ aryl)" refers to a 5 to 10 membered aryl that is attached to a parent moiety via a one to three membered alkyl chain.

The term "heteroaryl" as used herein refers to a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "($C_1$-$C_n$ alkyl)($C_5$-$C_6$heteroaryl)" refers to a 5 or 6 membered heteroaryl that is attached to a parent moiety via a one to "n" membered alkyl chain.

As used herein the term "patient" without further designation is intended to encompass any warm blooded vertebrate domesticated animal (including for example, but not limited to livestock, horses, cats, dogs and other pets) and humans.

EMBODIMENTS

The present disclosure is directed to insulin analogs that retain high activity at the insulin and/or IGF-1 receptor relative to native insulin. In one embodiment the insulin analogs comprise a modification of the tyrosine residue present at position 19 of the A chain of native insulin, wherein the analogs retain the activity of native insulin. Such analogs are referred to herein as "A19 insulin analogs". A19 insulin analogs may comprise additional modifications relative to native insulin peptide, wherein the insulin analog exhibits 70%, 80%, 90%, 95%, 100% or greater activity at the insulin receptor relative to native insulin.

In one embodiment an insulin derivative is prepared wherein an amino group is inserted into the peptide within the active site of insulin without loss in potency. More particularly, the selective substitution of a 4-amino phenyl amino acid moiety for the native tyrosine at position 19 of the A chain can be accommodated without loss in potency of the insulin peptide. Subsequent chemical amidation of this active site amino group with a prodrug moiety would dramatically lessen activity and thus provide a suitable prodrug of insulin.

In one embodiment the A19 insulin analog comprises one or more additional amino acid substitutions, relative to native insulin, at positions selected from A5, A8, A9, A10, A14, A15, A17, A18, A21, B1, B2, B3, B4, B5, B9, B10, B13, B14, B17, B20, B22, B23, B26, B27, B28, B29 and B30, and in one embodiment those amino acid substitutions are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

In one embodiment the A19 insulin analog comprises a substitution of an amino or methoxy group for the hydroxyl group present on the aromatic ring of the native tyrosine residue, and further comprises one to fifteen, one to ten, one to eight, one to five, or one to three amino acid substitutions at positions selected from A5, A8, A9, A10, A14, A15, A17, A18, B1, B2, B3, B4, B5, B13, B14, B17, B20, B22, B23, B26, B27, B28, B29 and B30. In one embodiment the A19 insulin analog comprises one to ten, one to eight, one to five, or one to three amino acid substitutions at positions selected from A5, A8, A9, A10, A14, A15, A17, A18, B1, B2, B3, B4, B5, B13, B14, B17, B20, B22, B23, B26, B27, B28, B29 and B30, wherein the analog is further modified, relative to the native insulin sequence, by one or more deletions of amino acids from positions B1-4 and B26-30 of the native insulin B peptide. In another embodiment the A19 insulin analog comprises one to eight, one to five, or one to three amino acid substitutions at positions selected from A5, A8, A9, A10, A14, A15, A17, A18, B1, B2, B3, B4, B5, B13, B14, B17, B20, B22, B23, B26, B27, B28, B29 and B30, and is further modified, relative to the native insulin sequence, by the deletion of amino acids B1-4 and/or B26-30.

In one embodiment the A19 insulin comprises a substitution of an amino or methoxy group for the hydroxyl group present on the aromatic ring of the native tyrosine residue, and further comprises an amino acid substitution at position A8 (relative to the native insulin peptide) with an amino acid selected from the group consisting of histidine, arginine and lysine. In a further embodiment the amino acid at B10 is an amino acid selected from the group consisting of aspartic acid, glutamic acid, homoglutamic acid, homocysteic acid and cysteic acid. In one embodiment the A19 insulin analog comprises a substitution of an amino or methoxy group for the hydroxyl group present on the aromatic ring of the native tyrosine residue, and further comprises an amino acid substitution, relative to the native insulin peptide, of an amino acid at a position selected from the group consisting of A8 and B28-30.

In accordance with one embodiment an insulin analog is provided comprising an A chain polypeptide comprising the sequence GIVEQCC$X_1$SICSLYQLEN$X_2$C$X_3$ (SEQ ID NO: 3), wherein $X_1$ is selected from the group consisting of threonine and histidine;

$X_2$ is an amino acid of the general structure

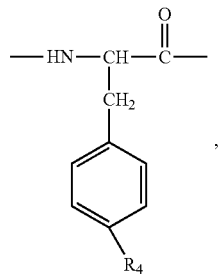

wherein $R_4$ is $NH_2$ or $OCH_3$; and $X_3$ is asparagine, glycine, alanine, threonine, or serine, or an analog thereof comprising a sequence that differs from SEQ ID NO: 3 by 1 to 9, 1 to 5 or 1 to 3 amino acid modifications, selected from positions A5, A8, A9, A10, A14, A15, A17, A18. In one embodiment $R_4$ is $NH_2$. In a further embodiment $X_1$ is threonine, $X_3$ is asparagine and $R_4$ is $NH_2$.

More particularly, in one embodiment an A19 insulin analog is provided comprising an A chain sequence of GIVEQCCX$_1$SICSLYQLENX$_2$CX$_3$ (SEQ ID NO: 3) and a B chain sequence comprising a sequence of X$_4$LCGX$_5$X$_6$LVEALYLVCG ERGFF (SEQ ID NO: 4) wherein $X_1$ is selected from the group consisting of threonine and histidine;

$X_2$ is an amino acid of the general structure

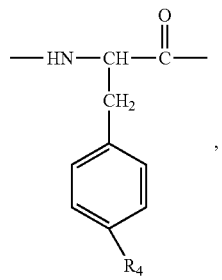

wherein $R_4$ is $NH_2$ or $OCH_3$;

$X_3$ is asparagine or glycine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid, or an analog thereof wherein SEQ ID NO: 3 and/or SEQ ID NO: 4 independently differs from the respective SEQ ID NO: 3 and/or SEQ ID NO: 4 sequence by 1 to 3 amino acid modifications, selected from positions A5, A8, A9, A10, A14, A15, A17, A18, A5, A8, A9, A10, A12, A14, A15, A17, A18, B1, B2, B3, B4, B5, B13, B14, B17, B20, B22, B23, B26, B27, B28, B29 and B30.

In another embodiment an A19 insulin analog is provided comprising an A chain sequence of GIVEQCCX$_1$SICSLYQLENX$_2$CX$_3$ (SEQ ID NO: 3) and a B chain sequence comprising a sequence of X$_{11}$VNQX$_4$LCGX$_5$X$_6$LVEALYLVCGERGFFYTX$_9$ X$_{10}$ (SEQ ID NO: 5) wherein $X_1$ is selected from the group consisting of threonine, histidine, arginine and lysine;

$X_2$ is an amino acid of the general structure

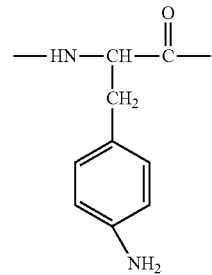

$X_3$ is asparagine or glycine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_9$ is aspartate-lysine, a lysine-proline dipeptide, or a proline-lysine dipeptide;

$X_{10}$ is threonine or a theonine-arginine-arginine tripeptide;

$X_{11}$ is selected from the group consisting of phenylalanine and desamino-phenylalanine. In one embodiment the B chain sequence comprises the sequence HLCG-SHLVEALYLVCGERGFF (SEQ ID NO: 7) and in a further embodiment the B chain is selected from the group consisting of FVNQHLCGSHLVEALYLVCGERGFFYTPKT (SEQ ID NO: 8), FVNQHLCGSHLVEALYLVCGERGFFYTKPT (SEQ ID NO: 9) and FVNQHLCGSHLVEALYLVCGERG-FFYTPKTRR (SEQ ID NO: 10). In a further embodiment, an A19 insulin analog is provided comprising an A chain sequence of GIVEQCCX$_1$SICSLYQLENX$_2$CX$_3$ (SEQ ID NO: 3) and a B chain sequence comprising a sequence selected from the group consisting of SEQ ID NO: 7, SEQ ID NO: 8, and SEQ ID NO: 9, wherein $X_1$ is selected from the group consisting of threonine and histidine, $X_2$ is an amino acid of the general structure

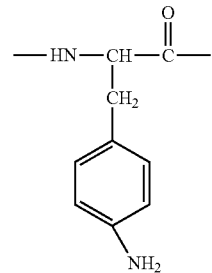

and $X_3$ is asparagine, and in one embodiment, $X_1$ is threonine, $X_2$ is 4-amino phenylalanine and $X_3$ is asparagine.

In one embodiment an A19 insulin analog is provided comprising an A chain sequence of GIVEQCCX$_1$SICSLYQLENX$_2$CX$_3$ (SEQ ID NO: 3) and a B chain sequence comprising a sequence of FVNQHLCG-SHLVEALYLVCGERGFFYTPKT (SEQ ID NO: 8) or FVN-QHLCGSHLVEALYLVCGERGFFYTKPT (SEQ ID NO: 9), wherein $X_1$ is selected from the group consisting of threonine and histidine;

$X_2$ is an amino acid of the general structure

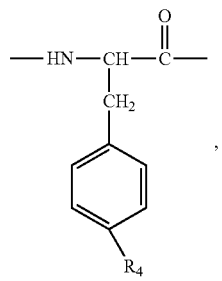

wherein $R_4$ is $NH_2$ or $OCH_3$; and $X_3$ is asparagine or glycine. In a further embodiment, $R_4$ is $NH_2$ and $X_3$ is asparagine, and in one embodiment, $R_4$ is $NH_2$, $X_1$ is threonine and $X_3$ is asparagine.

In accordance with one embodiment a single-chain insulin analog is provided wherein the A19 amino acid has been substituted with an amino acid of the general structure

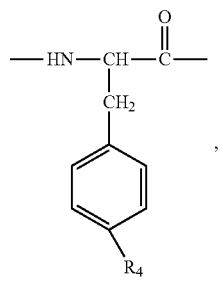

wherein $R_4$ is $NH_2$ or $OCH_3$. In accordance with one embodiment the single-chain insulin analog comprises a compound of the formula: B-P-A19, wherein: B represents the B-chain of insulin or a functional analog thereof, A19 represents an A19 A chain analog as disclosed herein, and P represents a linker, including a peptide linker, that covalently joins the amino-terminus of the A chain to the carboxy-terminus of the B chain. In one embodiment the linker is a peptide linker of about 5 to about 18, or about 10 to about 14, or about 4 to about 8, or about 6 amino acids.

In one embodiment the single chain insulin analog comprises a compound of the formula: B-P-A19, wherein:

B represents a B chain sequence comprising a sequence of $X_4LCGX_5X_6LVEALYLVCG$ ERGFF (SEQ ID NO: 4);

A19 represents an A chain sequence comprising a sequence of GIVEQCCX$_1$SICSLYQLENX$_2$CX$_3$ (SEQ ID NO: 3); and P represents a peptide linker of 4 to 8 amino acids, further wherein $X_1$ is selected from the group consisting of threonine and histidine;

$X_2$ is an amino acid of the general structure

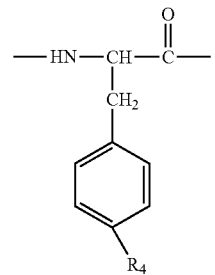

wherein $R_4$ is $NH_2$ or $OCH_3$;

$X_3$ is asparagine or glycine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid. In accordance with one embodiment the peptide linker is 5 to 18 amino acids in length and comprises a sequence selected from the group consisting of: Gly-Gly-Gly-Pro-Gly-Lys-Arg (SEQ ID NO: 11), Gly-Tyr-Gly-Ser-Ser-Ser-Arg-Arg-Ala-Pro-Gln-Thr (SEQ ID NO: 12), Arg-Arg-Gly-Pro-Gly-Gly-Gly (SEQ ID NO: 21), Gly-Gly-Gly-Gly-Gly-Lys-Arg (SEQ ID NO: 13), Arg-Arg-Gly-Gly-Gly-Gly-Gly (SEQ ID NO: 14), Gly-Gly-Ala-Pro-Gly-Asp-Val-Lys-Arg (SEQ ID NO: 15), Arg-Arg-Ala-Pro-Gly-Asp-Val-Gly-Gly (SEQ ID NO: 16), Gly-Gly-Tyr-Pro-Gly-Asp-Val-Lys-Arg (SEQ ID NO: 17), Arg-Arg-Tyr-Pro-Gly-Asp-Val-Gly-Gly (SEQ ID NO: 18), Gly-Gly-His-Pro-Gly-Asp-Val-Lys-Arg (SEQ ID NO: 19) and Arg-Arg-His-Pro-Gly-Asp-Val-Gly-Gly (SEQ ID NO: 20).

In one embodiment the peptide linker comprises a sequence selected from the group consisting of AGRGSGK (SEQ ID NO: 24), AGLGSGK (SEQ ID NO: 25), AGMGSGK (SEQ ID NO: 26), ASWGSG-K (SEQ ID NO: 27), TGLGSGQ (SEQ ID NO: 28), TGLGRGK (SEQ ID NO: 29), TGLGSGK (SEQ ID NO: 30), FIGLYSGK (SEQ ID NO: 31), KGLSSGQ (SEQ ID NO: 32), VGLMSGK (SEQ ID NO: 33), VGLSSGQ (SEQ ID NO: 34), VGLYSGK (SEQ ID NO: 35), VGLSSGK (SEQ NO: 36), VGMSSGK (SEQ ID NO: 37), VWSSSGK (SEQ ID NO: 38), VGSSSGK (SEQ ID NO: 39), VGMSSGK (SEQ ID NO: 40), TGLGSGR (SEQ ID NO: 41), TGLGKGQ (SEQ ID NO: 42), KGLSSGQ (SEQ ID NO: 43), VKLSSGQ (SEQ ID NO: 44), VGLKSGQ (SEQ ID NO: 45), TGLGKGQ (SEQ ID NO: 46) and VGLSKGQ (SEQ ID NO: 47), In one embodiment the peptide linker is 7 to 12 amino acids in length and comprises the sequence Gly-Gly-Gly-Pro-Gly-Lys-Arg (SEQ ID NO: 11) or Gly-Tyr-Gly-Ser-Ser-Ser-Arg-Arg-Ala-Pro-Gln-Thr (SEQ ID NO: 12).

In one embodiment the single-chain insulin analog has the amino acid sequence:

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr-Gly-Pro-Leu-Ala-Leu-Glu-Gly-Ser-Leu-Gln-Lys-Arg-Gly-Ile-Val-Glu-Gln-Cys-Cys-Thr-Ser-Ile-Cys-Ser-Leu-Tyr-Gln-Leu-Glu-Asn-Xaa-Cys-Asn (SEQ ID NO: 23) wherein Xaa is an amino acid of the general structure

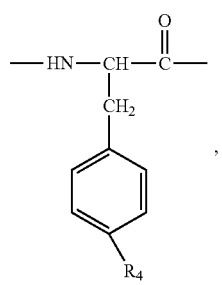

wherein R$_4$ is NH$_2$ or OCH$_3$.

The A19 insulin analogs disclosed herein can be further modified to improve the peptide's solubility in aqueous solutions at physiological pH, while enhancing the effective duration of the peptide by preventing renal clearance of the peptide. Peptides are easily cleared because of their relatively small molecular size when compared to plasma proteins. Increasing the molecular weight of a peptide above 40 kDa exceeds the renal threshold and significantly extends duration in the plasma. Accordingly, in one embodiment the A19 insulin analogs are further modified to comprise a covalently linked hydrophilic moiety. In one embodiment the hydrophilic moiety is a plasma protein, a polyethylene chain or the Fc portion of an immunoglobin. Therefore, in one embodiment the presently disclosed A19 insulin analogs are further modified to comprise one or more hydrophilic groups covalently linked to the side chains of amino acids.

In accordance with one embodiment the A19 insulin analogs disclosed herein are modified by linking a hydrophilic moiety to either the N-terminal amino acid of the B chain or to the side chain of a lysine amino acid located at the carboxy terminus of the B chain, including for example, at position 28 of SEQ ID NO: 9 or at position 29 of SEQ ID NO: 8. In one embodiment a single-chain insulin analog is provided wherein one of the amino acids of the peptide linker is modified by linking a hydrophilic moiety to the side chain of the peptide linker. In one embodiment the modified amino acid is cysteine, lysine or acetyl phenylalanine. In one embodiment the peptide linker is selected from the group consisting of TGLGSGQ (SEQ ID NO:28), VGLSSGQ (SEQ ID NO:34), VGLSSGK (SEQ ID NO:36), TGLGSGR (SEQ ID NO: 41), TGLGKGQ (SEQ ID NO: 42), KGLSSGQ (SEQ ID NO: 43), VKLSSGQ (SEQ ID NO: 44), VGLKSGQ (SEQ ID NO: 45), TGLGKGQ (SEQ ID NO: 46) and VGLSKGQ (SEQ ID NO: 47) and the hydrophilic moiety (e.g., polyethylene glycol) is linked to the lysine side chain of the peptide linker. In another embodiment the A19 insulin analogs disclosed herein are further modified by the addition of a modified amino acid to the carboxy terminus of the B chain of the A19 insulin analogs, wherein the C-terminally added amino acid is modified to comprise a hydrophilic moiety linked to the amino acid. In one embodiment the amino acid added to the C-terminus is a modified cysteine, lysine or acetyl phenylalanine. In one embodiment the hydrophilic moiety is selected from the group consisting of a plasma protein, polyethylene oxide chain and an Fc portion of an immunoglobin.

In one embodiment the hydrophilic group is a polyethylene oxide chain, and in one embodiment two or more polyethylene oxide chains are covalently attached to two or more amino acid side chains of the A19 insulin analog. In accordance with one embodiment the hydrophilic moiety is covalently attached to an amino acid side chain of an A19 insulin analog disclosed herein at a position selected from the group consisting of A9, A14, A15, B22, B28, B29 and the C-terminus or N-terminus of the B chain. For A19 insulin analogs having multiple polyethylene oxide chains, the polyethylene oxide chains can be attached at the N-terminal amino acid of the B chain or to the side chain of a lysine amino acid located at the carboxy terminus of the B chain, or by the addition of a single amino acid at the C-terminus of the peptide wherein the added amino acid has a polyethylene oxide chain linked to its side chain.

In accordance with one embodiment, the A19 insulin analogs disclosed herein are further modified by amino acid substitutions, wherein the substituting amino acid comprises a side chain suitable for crosslinking with hydrophilic moieties, including for example, polyethylene glycol. In one embodiment the amino acid, at the position of the A19 insulin analog where the hydrophilic moiety is to be linked, is substituted (or added at the C-terminus) with a natural or synthetic amino acid to introduce, or allow for ease in attaching, the hydrophilic moiety. For example, in one embodiment a native amino acid at position selected from A5, A8, A9, A10, A12, A14, A15, A17, A18, B1, B2, B3, B4, B5, B13, B14, B17, B21, B22, B26, B27, B28, B29 and B30 is substituted with a lysine, cysteine or acetyl phenylalanine residue (or a lysine, cysteine or acetyl phenylalanine residue is added to the C-terminus) to allow for the covalent attachment of a polyethylene oxide chain.

In one embodiment the A19 insulin analog has a single cysteine residue added to the amino or carboxy terminus of the B chain, or the A19 insulin analog is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, the A19 insulin analog has a single lysine residue added to the carboxy terminus of the B chain, or the A19 insulin analog is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol.

In those embodiments where the A19 insulin analog comprises a polyethylene glycol chain, the polyethylene chain may be in the form of a straight chain or it may be branched. In accordance with one embodiment the polyethylene glycol chain has an average molecular weight selected from the range of about 20,000 to about 60,000 Daltons. Multiple polyethylene glycol chains can be linked to the A19 insulin analog to provide an A19 insulin analog with optimal solubility and blood clearance properties. In one embodiment the A19 insulin analog is linked to a single polyethylene glycol chain that has an average molecular weight selected from the range of about 20,000 to about 60,000 Daltons. In another embodiment the A19 insulin analog is linked to two polyethylene glycol chains wherein the combined average molecular weight of the two chains is selected from the range of about 40,000 to about 80,000 Daltons. In one embodiment a single polyethylene glycol chain having an average molecular weight of 20,000 or 60,000 Daltons is linked to the A19 insulin analog. In another embodiment a single polyethylene glycol chain is linked to the A19 insulin analog and has an average molecular weight selected from the range of about 40,000 to about 50,000 Daltons. In one embodiment two polyethylene glycol chains are linked to the A19 insulin analog wherein the first and second polyethylene glycol chains each have an average molecular weight of 20,000 Daltons. In another embodiment two polyethylene glycol chains are linked to the A19 insulin analog wherein the first and second polyethylene glycol chains each have an average molecular weight of 40,000 Daltons.

In a further embodiment an A19 insulin analog comprising two or more polyethylene glycol chains covalently bound to the peptide is provided, wherein the total molecular weight of the polyethylene glycol chains is about 40,000 to about 60,000 Daltons. In one embodiment the pegylated A19 insulin analog comprises a polyethylene glycol chain linked to one or more amino acids selected from the N-terminus of the B chain and/or position 28 of SEQ ID NO: 9 or at position 29 of SEQ ID NO: 8, wherein the combined molecular weight of the PEG chain(s) is about 40,000 to about 80,000 Daltons.

In accordance with one embodiment, an A19 insulin analog is provided wherein a plasma protein has been covalently linked to an amino acid side chain of the peptide to improve the solubility, stability and/or pharmacokinetics of the A19 insulin analog. For example, serum albumin can be covalently bound to the A19 insulin analogs presented herein. The plasma protein can be linked to the N-terminus of the B chain or at the C-terminus of the A or B chain. In one embodiment the plasma protein is covalently bound to the N-terminus of the B chain and/or to an amino acid corresponding to position 28 of SEQ ID NO: 9 or at position 29 of SEQ ID NO: 8.

In accordance with one embodiment, an A19 insulin analog is provided wherein a linear amino acid sequence representing the Fc portion of an immunoglobin molecule has been covalently linked to an amino acid side chain of an A19 insulin analog disclosed. Attachment of the Fc portion is made to improve the solubility, stability and/or pharmacokinetics of theA19 insulin analog. The Fc portion can be linked to the N-terminus of the B chain or at the C-terminus of the A or B chain. For example, the amino acid sequence representing the Fc portion of an immunoglobin molecule can be covalently bound to the C-terminus of the B chain, including for example linkage to an amino acid corresponding to position 28 of SEQ ID NO: 9 or at position 29 of SEQ ID NO: 8. The Fc portion is typically one isolated from IgG, but the Fc peptide fragment from any immunoglobin should function equivalently.

In a specific aspect of the invention, the A19 insulin analog is modified to comprise an acyl group by direct acylation of an amine, hydroxyl, or thiol of a side chain of an amino acid of the A19 insulin analog. In some embodiments, the A19 insulin analog is directly acylated through the side chain amine, hydroxyl, or thiol of an amino acid. In some embodiments, acylation is at one or more positions selected from A9, A14, A15, B22, B28 or B29. In this regard, the acylated A19 insulin analog can comprise an A chain amino acid sequence of SEQ ID NO: 3 and a B chain of SEQ ID NO: 5, or a modified amino acid sequence of SEQ ID NO: 3 and/or SEQ ID NO: 5 with at least one of the amino acids at positions A9, A14, A15, B22, B28 or B29 modified to any amino acid comprising a side chain amine, hydroxyl, or thiol. In some specific embodiments, the direct acylation of the A19 insulin analog occurs through the side chain amine, hydroxyl, or thiol of the amino acid at position B28 or B29. In one further embodiment the A19 insulin analog comprises an acyl group of a carboxylic acid with 1-24 carbon atoms bound to the epsilon-amino group of a Lys present at position B28 or B29.

In one embodiment a single-chain insulin analog of the general formula B-P-A19 is provided wherein one of the amino acids of the peptide linker is modified to comprise an acyl group by direct acylation of an amine, hydroxyl, or thiol of a side chain of an amino acid of the peptide linker. In accordance with one embodiment the peptide linker of the single-chain insulin analog is selected from the group consisting of AGRGSGK (SEQ ID NO: 24). AGLGSGK (SEQ ID NO: 25), AGMGSGK (SEQ ID NO: 26), ASWGSGK (SEC) ID NO: 27), TGLGSGQ (SEQ ID NO: 28). TGLGRGK (SEQ ID NO: 29), TGLGSGK (SEQ ID NO: 30), HGLYSGK (SEQ ID NO: 31), KGLGSGQ (SEC) ID NO: 32), VGLMSGK (SEQ ID NO: 33), VGLSSGQ (SEQ ID NO: 34), VGLYSGK (SEQ ID NO: 35), VGLSSGK (SEQ ID NO: 36), VGMSSGK (SEQ ID NO: 37), VWSSSGK (SEQ ID NO: 38), VGSSSGK (SEQ ID 39), VGMSSGK (SEQ ID NO: 40), TGLGSGR (SEQ ID NO: 41), TGLGKGQ (SEQ ID NO: 42), KGLSSGQ (SEQ ID NO: 43), VKLSSGQ (SEQ ID NO: 44), VGLKSGQ (SEQ ID NO: 45), TGLGKGQ (SEQ ID NO: 46) and VGLSKGQ (SEQ ID NO: 47) wherein at least one lysine residue in the A-chain, in the B-chain or in the connecting peptide has been chemically modified by acylation. In one embodiment the acylating group comprises a 1-5, 10-12 or 12-24 carbon chain.

The present disclosure also encompasses other conjugates in which A19 insulin analogs of the invention are linked, optionally via covalent bonding, and optionally via a linker, to a conjugate. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

An A19 insulin analog of the present disclosure can be linked to conjugate moieties via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through linkers or intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Exemplary conjugate moieties include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising an A19 insulin analog of the present disclosure and a plasma protein, wherein the plasma protein is selected from the group consisting of albumin, transferin and fibrinogen. In one embodiment the plasma protein moiety of the conjugate is albumin or transferin. In some embodiments, the A19 insulin analog is bound to the conjugate moiety via a linker, wherein the linker linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

The disclosed A19 insulin analogs are believed to be suitable for any use that has previously been described for insulin peptides. Accordingly, the A19 insulin analogs described herein can be used to treat hyperglycemia, or treat other metabolic diseases that result from high blood glucose levels. Accordingly, the present invention encompasses pharmaceutical compositions comprising an A19 insulin analog of the present disclosure, and a pharmaceutically acceptable carrier for use in treating a patient suffering from high blood glucose levels. In accordance with one embodiment the patient to be treated using the A19 insulin analogs disclosed herein is a domesticated animal, and in another embodiment the patient to be treated is a human.

One method of treating hyperglycemia in accordance with the present disclosure comprises the steps of administering the presently disclosed A19 insulin analog to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the A19 insulin analog composition is prepackaged in a syringe.

The A19 insulin analogs of the invention may be administered alone or in combination with other anti-diabetic agents. Anti-diabetic agents known in the art or under investigation include native insulin, native glucagon and functional derivatives thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the A19 insulin analogs disclosed herein can be formulated and administered to patients using standard pharmaceutically acceptable carriers and routes of administration known to those skilled in the art. Accordingly, the present disclosure also encompasses pharmaceutical compositions comprising one or more of the A19 insulin analogs disclosed herein, or a pharmaceutically acceptable salt thereof, in combination with a pharmaceutically acceptable carrier. In one embodiment the pharmaceutical composition comprises a 1 mg/ml concentration of the A19 insulin analog at pH of about 4.0 to about 7.0 in a phosphate buffer system. The pharmaceutical compositions may comprise the A19 insulin analog as the sole pharmaceutically active component, or the A19 insulin analog can be combined with one or more additional active agents. In accordance with one embodiment a pharmaceutical composition is provided comprising one of the A19 insulin analogs disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain an A19 insulin analog wherein the resulting active peptide is present at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various containers.

The compounds of the present invention can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

All therapeutic methods, pharmaceutical compositions, kits and other similar embodiments described herein contemplate that A19 insulin analogs include all pharmaceutically acceptable salts thereof.

In one embodiment the kit is provided with a device for administering the A19 insulin analog composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the insulin analog composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

Example 1

Synthesis of Insulin A & B Chains

Insulin A & B chains were synthesized on 4-methylbenzhyryl amine (MBHA) resin or 4-Hydroxymethyl-phenylacetamidomethyl (PAM) resin using Boc chemistry. The peptides were cleaved from the resin using HF/p-cresol 95:5 for 1 hour at 0° C. Following HF removal and ether precipitation, peptides were dissolved into 50% aqueous acetic acid and lyophilized. Alternatively, peptides were synthesized using Fmoc chemistry. The peptides were cleaved from the resin using Trifluoroacetic acid (TFA)/Triisopropylsilane (TIS)/ $H_2O$ (95:2.5:2.5), for 2 hour at room temperature. The peptide was precipitated through the addition of an excessive amount of diethyl ether and the pellet solubilized in aqueous acidic buffer. The quality of peptides were monitored by RP-HPLC and confirmed by Mass Spectrometry (ESI or MALDI).

Insulin A chains were synthesized with a single free cysteine at amino acid 7 and all other cysteines protected as acetamidomethyl A-(SH)[7](Acm)[6,11,20]. Insulin B chains were synthesized with a single free cysteine at position 7 and the other cysteine protected as acetamidomethyl B-(SH)[7] (Acm)[19]. The crude peptides were purified by conventional RP-HPLC.

The synthesized A and B chains were linked to one another through their native disulfide bond linkage in accordance with the general procedure outlined in FIG. 1. The respective B chain was activated to the $Cys^7$-Npys derivative through dissolution in DMF or DMSO and reacted with 2,2'-Dithiobis (5-nitropyridine) (Npys) at a 1:1 molar ratio, at room temperature. The activation was monitored by RP-HPLC and the product was confirmed by ESI-MS.

Figure 2:
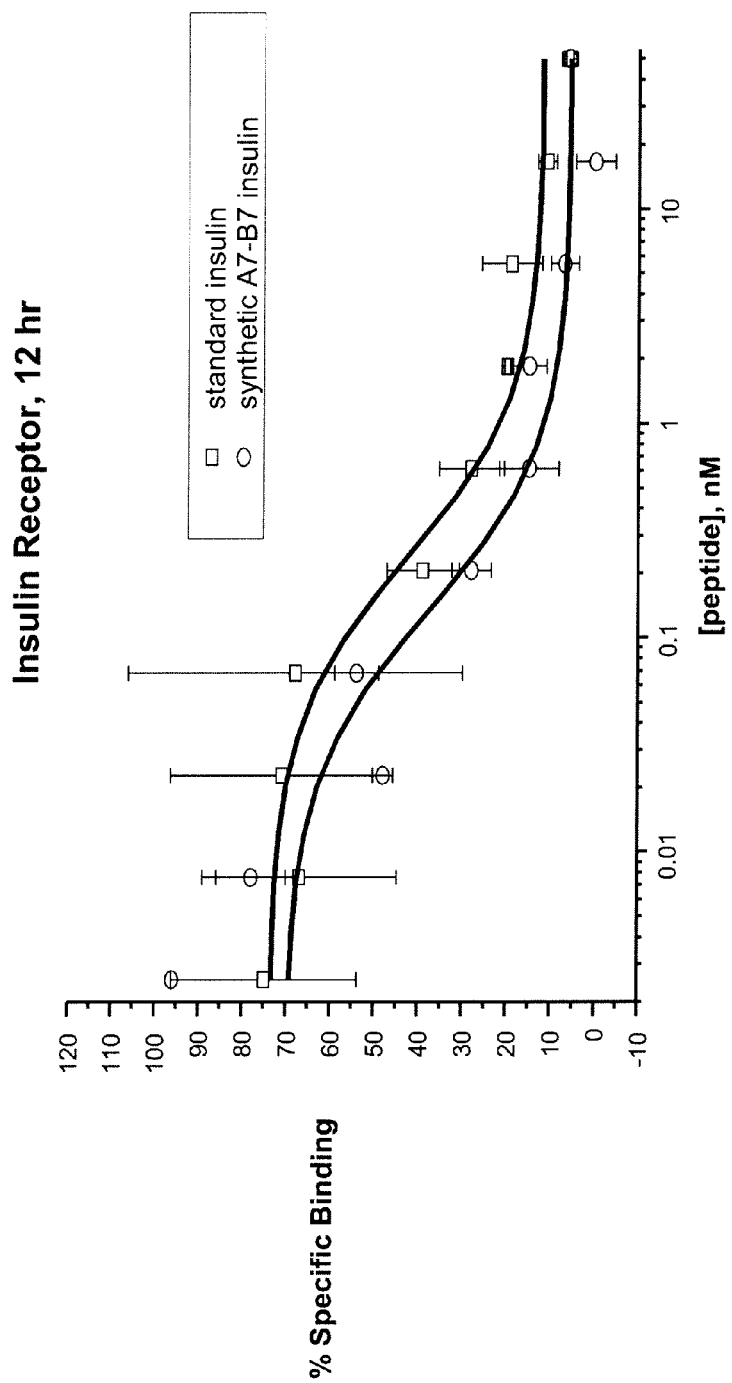

The first B7-A7 disulfide bond was formed by dissolution of the respective A-(SH)[7](Acm)[6,11,20] and B-(Npys)[7] (Acm)[19] at 1:1 molar ratio to a total peptide concentration of 10 mg/ml. When the chain combination reaction was complete the mixture was diluted to a concentration of 50% aqueous acetic acid. The last two disulfide bonds were formed simultaneously through the addition of iodine. A 40 fold molar excess of iodine was added to the solution and the mixture was stirred at room temperature for an additional hour. The reaction was terminated by the addition of an aqueous ascorbic acid solution. The mixture was purified by RP-HPLC and the final compound was confirmed by MALDI-MS. As shown in FIG. 2 and the data in Table 1, the synthetic insulin prepared in accordance with this procedure compares well with purified insulin for insulin receptor binding.

Insulin peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 1

Activity of synthesized insulin relative to native insulin

|  | Insulin Standard | | A7-B7 Insulin | |
| --- | --- | --- | --- | --- |
|  | AVER. | STDEV | AVER. | STDEV |
| $IC_{50}$ (nM) | 0.24 | 0.07 | 0.13 | 0.08 |
| % of Insulin Activity | 100 | | 176.9 | |

Example 2

Pegylation of Amine Groups (N-Terminus and Lysine) by Reductive Alkylation a. Synthesis Insulin (or an insulin analog), mPEG20k-Aldyhyde, and $NaBH_3CN$, in a molar ratio of 1:2:30, were dissolved in acetic acid buffer at a pH of 4.1-4.4. The reaction solution was composed of 0.1 N NaCl, 0.2 N acetic acid and 0.1 N $Na_2CO_3$. The insulin peptide concentration was approximately 0.5 mg/ml. The reaction occurs over six hours at room temperature. The degree of reaction completion was monitored by RP-HPLC and the yield of the reaction was approximately 50%.

b. Purification

The reaction mixture was diluted 2-5 fold with 0.1% TFA and applied to a preparative RP-HPLC column. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was eluted at approximately 35% buffer B. The desired compounds were verified by MAIDI-TOF, following chemical modification through sulftolysis or trypsin degradation.

Pegylation of Amine Groups (N-Terminus and Lysine) by N-Hydroxysuccinimide Acylation.

a. Synthesis

Insulin (or an insulin analog) along with mPEG20k-NHS were dissolved in 0.1 N Bicine buffer (pH 8.0) at a molar ratio of 1:1. The insulin peptide concentration was approximately 0.5 mg/ml. Reaction progress was monitored by HPLC. The yield of the reaction is approximately 90% after 2 hours at room temperature.

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was collected at approximately 35% B. The desired compounds were verified by MAIDI-TOF, following chemical modification through sulftolysis or trypsin degradation.

Reductive Aminated Pegylation of Acetyl Group on the Aromatic Ring of the Phenylalanine a. Synthesis Insulin (or an insulin analogue), mPEG20k-Hydrazide, and $NaBH_3CN$ in a molar ratio of 1:2:20 were dissolved in acetic acid buffer (pH of 4.1 to 4.4). The reaction solution was composed of 0.1 N NaCl, 0.2 N acetic acid and 0.1 N $Na_2CO_3$. Insulin or insulin analogue concentration was approximately 0.5 mg/ml. at room temperature for 24 h. The reaction process was monitored by HPLC. The conversion of the reaction was approximately 50%. (calculated by HPLC)

b. Purification

The reaction mixture was diluted 2-5 fold and loaded to RP-HPLC.

HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin, or the PEG-insulin analogue was collected at approximately 35% B. The desired compounds were verified by MAIDI-TOF, following chemical modification through sulftolysis or trypsin degradation.

Example 3

Insulin Receptor Binding Assay

The affinity of each peptide for the insulin or IGF-1 receptor was measured in a competition binding assay utilizing scintillation proximity technology. Serial 3-fold dilutions of the peptides were made in Tris-Cl buffer (0.05 M Tris-HCl, pH 7.5, 0.15 M NaCl, 0.1% w/v bovine serum albumin) and mixed in 96 well plates (Corning Inc., Acton, Mass.) with 0.05 nM (3-[125I]-iodotyrosyl) A TyrA14 insulin or (3-[125I]-iodotyrosyl) IGF-1 (Amersham Biosciences, Piscataway, N.J.). An aliquot of 1-6 micrograms of plasma membrane fragments prepared from cells over-expressing the human insulin or IGF-1 receptors were present in each well and 0.25 mg/well polyethylene imine-treated wheat germ agglutinin type A scintillation proximity assay beads (Amersham Biosciences, Piscataway, N.J.) were added. After five minutes of shaking at 800 rpm the plate was incubated for 12 h at room temperature and radioactivity was measured with MicroBeta1450 liquid scintillation counter (Perkin-Elmer, Wellesley, Mass.). Non-specifically bound (NSB) radioactivity was measured in the wells with a four-fold concentration excess of "cold" native ligand than the highest concentration in test samples. Total bound radioactivity was detected in the wells with no competitor. Percent specific binding was calculated as following: % Specific Binding=(Bound-NSB/Total bound-NSB)×100. IC50 values were determined by using Origin software (OriginLab, Northampton, Mass.).

Example 4

Insulin Receptor Phosphorylation Assay

To measure receptor phosphorylation of insulin or insulin analog, receptor transfected HEK293 cells were plated in 96 well tissue culture plates (Costar #3596, Cambridge, Mass.) and cultured in Dulbecco's modified Eagle medium (DMEM) supplemented with 100 IU/ml penicillin, 100 µg/ml streptomycin, 10 mM HEPES and 0.25% bovine growth serum (HyClone SH30541, Logan, Utah) for 16-20 hrs at 37° C., 5% $CO_2$ and 90% humidity. Serial dilutions of insulin or insulin analogs were prepared in DMEM supplemented with 0.5% bovine serum albumin (Roche Applied Science #100350, Indianapolis, Ind.) and added to the wells with adhered cells. After 15 min incubation at 37° C. in humidified atmosphere with 5% $CO_2$ the cells were fixed with 5% paraformaldehyde for 20 min at room temperature, washed twice with phosphate buffered saline pH 7.4 and blocked with 2% bovine serum albumin in PBS for 1 hr. The plate was then washed three times and filled with horseradish peroxidase-conjugated antibody against phosphotyrosine (Upstate biotechnology #16-105, Temecula, Calif.) reconstituted in PBS with 2% bovine serum albumin per manufacturer's recommendation. After 3 hrs incubation at room temperature the plate was washed 4 times and 0.1 ml of TMB single solution substrate (Invitrogen, #00-2023, Carlbad, Calif.) was added to each well. Color development was stopped 5 min later by adding 0.05 ml 1 N HCl. Absorbance at 450 nm was measured on Titertek Multiscan MCC340 (ThermoFisher, Pittsburgh, Pa.). Absorbance vs. peptide concentration dose response curves were plotted and $EC_{50}$ values were determined by using Origin software (OriginLab, Northampton, Mass.).

Example 5

Figure 3:
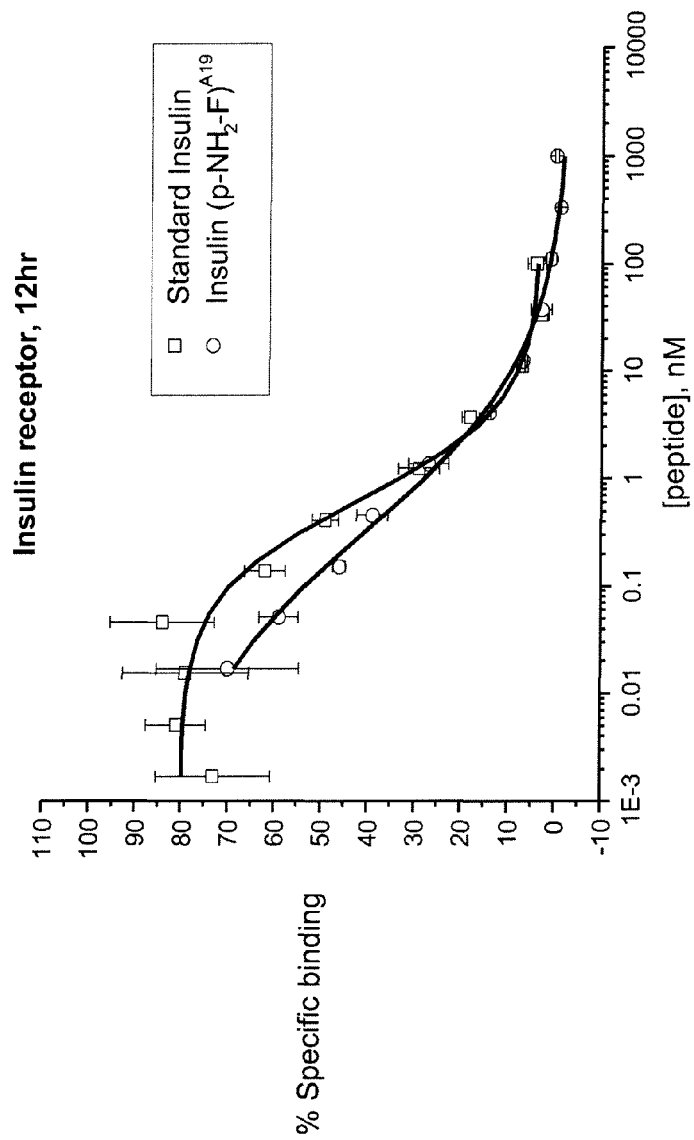

Specific analogs of insulin at A19 have been synthesized and characterized for their activity at the insulin receptors. Two highly active structural analogs have been identified at A19, wherein comparable structural changes at a second active site aromatic residue (B24) were not successful in identification of similarly full activity insulin analogs. Tables 2 and 3 illustrate the high structural conservation at position A19 for full activity at the insulin receptor. Table 2 demonstrates that only two insulin analogs with modifications at A19 have receptor binding activities similar to native insulin. For the 4-aminoPhe insulin analog, data from three separate experiments are provided. The column labeled "Activity (in test)" compares the percent binding of the insulin analog relative to native insulin for two separate experiments conducted simultaneously. The column labeled "Activity (0.60 nM)" is the relative percent binding of the insulin analog relative to the historical average value obtained for insulin binding using this assay. In either analysis, two A19 insulin analogs (4-amino phenylalanine and 4-methoxy phenylalanine) demonstrate receptor binding approximately equivalent to native insulin. FIG. 3 represents a graph demonstrating the respective specific binding of native insulin and the A19 insulin analog to the insulin receptor. Table 3 presents data showing that the two A19 insulin analogs (4-amino and 4-methoxy) that demonstrate equivalent binding activities as native insulin, also demonstrate equivalent phosphorylation activity at the insulin receptor.

TABLE 2

Insulin Receptor Binding Activity of A19 Insulin Analogs

| | Insulin Receptor | | | |
|---|---|---|---|---|
| Analogue | $IC_{50}$ | STDev | % native ligand Activity (in test) | % native ligand Activity (0.60 nM) |
| 4-OH (native insulin) | 0.64 | 0.15 | 100.0 | 100.0 |
| 4-COCH$_3$ | 31.90 | 9.47 | 0.60 | 1.90 |
| 4-NH$_2$ | 0.31 | 0.12 | 203.0 | 193.5 |
| | 0.83 | 0.15 | 103.0 | 72.3 |
| | 0.80 | 0.10 | 94.0 | 75.0 |
| 4-NO$_2$ | 215.7 | 108.01 | 0.30 | 1.30 |
| 3,4,5-3F | 123.3 | 31.10 | 0.50 | 0.50 |
| 4-OCH$_3$ | 0.5 | 0.50 | 173.0 | 120.0 |
| 3-OCH$_3$ | 4.74 | 1.09 | 28.0 | 12.7 |
| | 5.16 | 3.88 | 18.0 | 11.6 |
| 4-OH, 3,5-2Br | 1807.2 | 849.7 | 0.0 | 0.0 |
| 4-OH, 3,5-2 NO$_2$ | 2346.2 | 338.9 | 0.0 | 0.0 |

TABLE 3

Insulin Receptor Phosphorylation Activity of A19 Insulin Analogs

| | Insulin Receptor | | | |
|---|---|---|---|---|
| Analogue | $EC_{50}$ | STDev | % native ligand Activity (in test) | % native ligand Activity |
| 4-OH (native insulin) | 1.22 | 0.40 | 100.0 | |
| 4-NH$_2$ | 0.31 | 0.14 | 393.5 | |
| 4-OCH$_3$ | 0.94 | 0.34 | 129.8 | |

The invention claimed is:

1. A high potency insulin analog comprising an A chain sequence of GIVEQCCX$_1$SICSLYQLENX$_2$CX$_3$ (SEQ ID NO: 3): and a B chain sequence of X$_{11}$VNQX$_4$LCGX$_5$X$_6$LVEALYLVCGERGFFYTX$_9$ X$_{10}$ (SEQ ID NO: 5), wherein X$_1$ is selected from the group consisting of threonine and histidine;

X$_2$ is an amino acid of the general structure

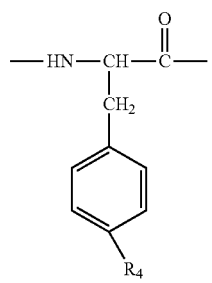

, wherein R$_4$ is NH$_2$ or OCH$_3$; and

X$_3$ is asparagine, glycine or alanine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid;

X$_9$ is aspartate-lysine dipeptide, a lysine-proline dipeptide, or a proline-lysine dipeptide;

X$_{10}$ is threonine, alanine, or a threonine-arginine-arginine tripeptide;

X$_{11}$ is selected from the group consisting of phenylalanine and desamino-phenylalanine or an analog thereof comprising a sequence that differs from SEQ ID NO: 3 and/or SEQ ID NO: 5 by 1 to 5 amino acid modifications, selected from amino acid substitutions at positions A5, A8, A9, A10, A14, A15, A17, A18, B1, B2, B3, B4, B5, B13, B14, B17, B20, B22, B23, B26, B27, B28, B29 and B30, or by the deletion of amino acids B1-4 and/or B26-30 wherein the insulin analog exhibits at least 70% activity at the insulin receptor relative to native insulin.

2. The insulin analog of claim 1 wherein R$_4$ is NH$_2$.

3. An insulin analog comprising an A chain sequence comprising a sequence of GIVEQCCX$_1$SICSLYQLENX$_2$CX$_3$ (SEQ ID NO: 3); and a B chain sequence comprising a sequence of X$_4$LCGX$_5$X$_6$LVEALYLVCGERGFF (SEQ ID NO: 4) wherein X$_1$ is selected from the group consisting of threonine and histidine;

X$_2$ is an amino acid of the general structure

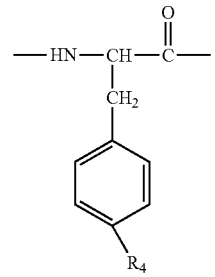

, wherein R$_4$ is NH$_2$ or OCH$_3$;

X$_3$ is asparagine or glycine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid.

4. The insulin analog of claim 3 wherein the B chain sequence comprises the sequence X$_{11}$VNQX$_4$LCGX$_5$X$_6$LVEALYLVCGERGFFYTX$_9$ X$_{10}$ (SEQ ID NO: 5) wherein X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid;

X$_9$ is aspartate-lysine dipeptide, a lysine-proline dipeptide, or a proline-lysine dipeptide;

X$_{10}$ is threonine, alanine, or a threonine-arginine-arginine tripeptide;

X$_{11}$ is selected from the group consisting of phenylalanine and desamino-phenylalanine.

5. The insulin analog of claim 3 wherein the A chain sequence comprises the sequence GIVEQCCTSICSLYQLENX$_2$CN (SEQ ID NO: 6) wherein X$_2$ is an amino acid of the general structure

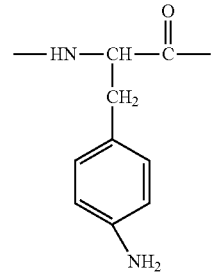

6. The insulin analog of claim 5 wherein the B chain sequence comprises the sequence HLCG-SHLVEALYLVCGERGFF (SEQ ID NO: 7).

7. The insulin analog of claim 5 wherein the B chain sequence comprises the sequence FVNQHLCG-SHLVEALYLVCGERGFFYTPKT (SEQ ID NO: 8).

8. The insulin analog of claim 5 wherein the B chain sequence comprises the sequence FVNQHLCG-SHLVEALYLVCGERGFFYTKPT (SEQ ID NO: 9).

9. The insulin analog of claim 3 further comprising a hydrophilic moiety is linked to an amino acid of the B chain.

10. The insulin analog of claim 9 wherein the hydrophilic moiety is linked to the N-terminal amino acid of the B chain.

11. The insulin analog of claim 7 wherein a hydrophilic moiety is linked to either the N-terminal amino acid of the B chain or to the amino acid at position 29 of SEQ ID NO: 8.

12. The insulin analog of claim 8 wherein a hydrophilic moiety is linked to either the N-terminal amino acid of the B chain or to the amino acid at position 28 of SEQ ID NO: 9.

13. The insulin analog of claim 9 wherein the hydrophilic moiety is polyethylene glycol.

14. A single chain insulin analog comprises a compound of the formula: B-P-A19, wherein:
B represents a sequence comprising a sequence of $X_4$LCG$X_5$$X_6$LVEALYLVCGERGFF (SEQ ID NO: 4);
A19 represents a sequence comprising a sequence of GIVEQCC$X_1$SICSLYQLEN$X_2$C$X_3$ (SEQ ID NO: 3); and
P represents a peptide linker of about 4 to about 14 amino acids, further wherein
$X_1$ is selected from the group consisting of threonine and histidine;
$X_2$ is an amino acid of the general structure

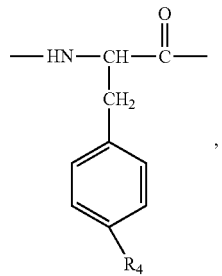

wherein $R_4$ is $NH_2$ or $OCH_3$;
$X_3$ is asparagine or glycine;
$X_4$ is selected from the group consisting of histidine and threonine;
$X_5$ is selected from the group consisting of alanine, glycine and serine;
$X_6$ is selected from the group consisting of histidine, aspartic acid, glutamic acid, homocysteic acid and cysteic acid.

15. The single chain insulin analog of claim 14 wherein the peptide linker is selected from the group consisting of
Gly-Gly-Gly-Pro-Gly-Lys-Arg (SEQ ID NO: 11), Gly-Tyr-Gly-Ser-Ser-Ser-Arg-Arg-Ala-Pro-Gln-Thr (SEQ ID NO: 12), Arg-Arg-Gly-Pro-Gly-Gly-Gly (SEQ ID NO: 21), Gly-Gly-Gly-Gly-Gly-Lys-Arg (SEQ ID NO: 13), Arg-Arg-Gly-Gly-Gly-Gly-Gly (SEQ ID NO: 14), Gly-Gly-Ala-Pro-Gly-Asp-Val-Lys-Arg (SEQ ID NO: 15), Arg-Arg-Ala-Pro-Gly-Asp-Val-Gly-Gly (SEQ ID NO: 16), Gly-Gly-Tyr-Pro-Gly-Asp-Val-Lys-Arg (SEQ ID NO: 17), Arg-Arg-Tyr-Pro-Gly-Asp-Val-Gly-Gly (SEQ ID NO: 18), Gly-Gly-His-Pro-Gly-Asp-Val-Lys-Arg (SEQ ID NO: 19) and Arg-Arg-His-Pro-Gly-Asp-Val-Gly-Gly (SEQ ID NO: 20).

16. The single chain insulin analog of claim 15 wherein $R_4$ is $NH_2$.

17. The single chain insulin analog of claim 14 wherein $R_4$ is $NH_2$;
the B chain comprises the sequence of $X_{11}$VNQ$X_4$LCG$X_5$$X_6$LVEALYLVCGERGFFYT$X_9$$X_{10}$ (SEQ ID NO: 5); and
the peptide linker is 4 to 8 amino acids in length, further wherein
$X_4$ is selected from the group consisting of histidine and threonine;
$X_5$ is selected from the group consisting of alanine, glycine and serine;
$X_6$ is selected from the group consisting of histidine, aspartic acid, glutamic acid, homocysteic acid and cysteic acid;
$X_9$ is aspartate-lysine dipeptide, a lysine-proline dipeptide, or a proline-lysine dipeptide;
$X_{10}$ is threonine, alanine, or a threonine-arginine-arginine tripeptide;
$X_{11}$ is selected from the group consisting of phenylalanine and desamino-phenylalanine.

18. The single chain insulin analog of claim 17 wherein the peptide linker comprises the sequence: GGGPGKR (SEQ ID NO: 11), AGRGSGK (SEQ ID NO: 24); AGLGSGK (SEQ ID NO: 25): AGMGSGK (SEQ ID NO: 26); ASWGSGK (SEQ ID NO: 27); TGLGSGQ (SEQ ID NO: 28); TGLGRGK (SEQ ID NO: 29); TGLGSGK (SEQ ID NO: 30); HGLYSGK (SEQ ID NO: 31); KGLGSGQ (SEQ ID NO: 32); VGLMSGK (SEQ ID NO: 33); VGLSSGQ (SEC) ID NO: 34); VGLYSGK (SEQ ID NO: 35), VGLSSGK (SEQ ID NO: 36); VGMSSGK (SEQ ID NO: 37) VWSSSGK (SEQ ID NO: 38), VGSSSGK (SEQ ID NO: 39), and VGMSSGK (SEQ ID NO: 40).

19. The insulin analog of claim 3 wherein a hydrophilic moiety is linked through an amino acid side chain at position A9, A14, A15, B22, B28, B29, the C-terminus or N-terminus of the B chain or a lysine side chain of the peptide linker.

20. The insulin analog of claim 3 wherein said analog is acylated at one or more positions selected from A9, A14, A15, B22, B28 or B29.

21. A pharmaceutical composition comprising the insulin analog of claim 3 and a pharmaceutically acceptable carrier.

22. A method of treating diabetes, said method comprising administering an effective amount of a pharmaceutical composition of claim 21.

* * * * *

UNITED STATES PATENT AND TRADEMARK OFFICE
CERTIFICATE OF CORRECTION

PATENT NO. : 8,481,485 B2
APPLICATION NO. : 13/130976
DATED : July 9, 2013
INVENTOR(S) : Richard D. DiMarchi and Jie Han It is certified that error appears in the above-identified patent and that said Letters Patent is hereby corrected as shown below:

In the Claims:

Claim 18, Column 48, line 40, delete "(SEC) ID NO: 34)" and insert -- (SEQ ID NO: 34) -- therefor.

Signed and Sealed this
Twelfth Day of November, 2013

Teresa Stanek Rea
*Deputy Director of the United States Patent and Trademark Office*